United States Patent
Saleh et al.

(10) Patent No.: US 12,094,608 B2
(45) Date of Patent: Sep. 17, 2024

(54) PATTERN RECOGNITION ENGINE FOR BLOOD GLUCOSE MEASUREMENTS

(71) Applicant: Sanofi, Paris (FR)

(72) Inventors: Milena Saleh, Frankfurt am Main (DE); Anton Petkov, Frankfurt am Main (DE); Jochen Sieber, Frankfurt am Main (DE); Giacomo Vespasiani, San Benedetto del Tronto (IT); Sandro Girolami, San Benedetto del Tronto (IT)

(73) Assignee: Sanofi, Paris (FR)

( * ) Notice: Subject to any disclaimer, the term of this patent is extended or adjusted under 35 U.S.C. 154(b) by 486 days.

(21) Appl. No.: 17/312,704

(22) PCT Filed: Dec. 17, 2019

(86) PCT No.: PCT/EP2019/085476
§ 371 (c)(1),
(2) Date: Jun. 10, 2021

(87) PCT Pub. No.: WO2020/127137
PCT Pub. Date: Jun. 25, 2020

(65) Prior Publication Data
US 2022/0051797 A1    Feb. 17, 2022

(30) Foreign Application Priority Data
Dec. 19, 2018   (EP) ..................... 18306744

(51) Int. Cl.
*G16H 50/20* (2018.01)
*A61B 5/145* (2006.01)
*G16H 10/40* (2018.01)

(52) U.S. Cl.
CPC ............ *G16H 50/20* (2018.01); *G16H 10/40* (2018.01); *A61B 5/14532* (2013.01)

(58) Field of Classification Search
CPC ............................... G16H 50/20; G16H 10/40
(Continued)

(56) References Cited

U.S. PATENT DOCUMENTS

| | | | |
|---|---|---|---|
| 2008/0234992 A1* | 9/2008 | Ray | G16H 20/10 703/2 |
| 2009/0095292 A1 | 4/2009 | Hamano et al. | |

(Continued)

FOREIGN PATENT DOCUMENTS

| | | |
|---|---|---|
| CN | 101290320 A | 10/2008 |
| CN | 104470430 A | 3/2015 |

(Continued)

OTHER PUBLICATIONS

Eason, Fenella; Doing Diabetes (Type 1): Symbiotic Ethics and Practices of Care Embodied in Human-Canine Collaborations and Olfactory Sensitivity; University of Exeter (United Kingdom), ProQuest Dissertations Publishing, 2017. 13872774. (Year: 2017).*

(Continued)

*Primary Examiner* — Hiep V Nguyen
(74) *Attorney, Agent, or Firm* — Fish & Richardson P.C.

(57) ABSTRACT

This specification relates to systems, methods and apparatus for recognising patterns in blood glucose measurements. According to a first aspect, this specification discloses a computer implemented blood glucose analysis method comprising: receiving a plurality of blood glucose measurements relating to an individual taken over a plurality of temporal frames; identifying hypoglycaemic and/or hyperglycaemic blood glucose measurements in the plurality of blood glucose measurements; identifying a plurality of sub-intervals of the temporal frames in which there are a number of hypoglycaemic and/or hyperglycaemic blood glucose measurements that satisfies a threshold condition; inferring a temporal relationship between blood glucose measurements (Continued)

in a first sub-interval of the identified sub-intervals and blood glucose measurements in a second sub-interval of the identified sub-intervals; outputting the identified one or more sub-intervals of the temporal frames; and outputting a suggested causal driver for the inferred temporal relationship.

17 Claims, 6 Drawing Sheets

(58) Field of Classification Search
USPC .................................................. 705/2
See application file for complete search history.

(56) References Cited

U.S. PATENT DOCUMENTS

| | | | |
|---|---|---|---|
| 2010/0047745 | A1 | 2/2010 | Bergqwist et al. |
| 2014/0024907 | A1 | 1/2014 | Howell et al. |
| 2020/0375505 | A1* | 12/2020 | Srinivasan ......... G08B 21/0492 |

FOREIGN PATENT DOCUMENTS

| | | | |
|---|---|---|---|
| CN | 104520862 A | 4/2015 | |
| CN | 107545928 A | 1/2018 | |
| CN | 108335750 A | 7/2018 | |
| EP | 2031534 A1 | 3/2008 | |
| EP | 1956371 | 8/2008 | |
| JP | 2007-301347 A | 11/2007 | |
| JP | 2008-229330 A | 10/2008 | |
| JP | 2017-225602 A | 12/2017 | |
| WO | WO 2007/116953 A1 | 10/2007 | |
| WO | WO 2013/184896 | 12/2013 | |
| WO | WO 2018/132507 | 7/2018 | |
| WO | WO 2018/178048 | 10/2018 | |
| WO | WO-2020002428 A1 * | 1/2020 | ......... A61B 5/14532 |

OTHER PUBLICATIONS

International Preliminary Report on Patentability in International Application No. PCT/EP2019/085476, dated Jun. 16, 2021, 11 pages.

International Search Report and Written Opinion in International Application No. PCT/EP2019/085476, dated Mar. 19, 2020, 14 pages.

* cited by examiner

PATTERN RECOGNITION ENGINE FOR BLOOD GLUCOSE MEASUREMENTS

CROSS-REFERENCE TO RELATED APPLICATIONS

The present application is the national stage entry of International Patent Application No. PCT/EP2019/085476, filed on Dec. 17, 2019, and claims priority to Application No. EP 18306744.6, filed on Dec. 19, 2018, the disclosures of which are incorporated herein by reference.

TECHNICAL FIELD

This specification relates to systems, methods and apparatus for recognising patterns in blood glucose measurements.

BACKGROUND

Review of self-monitoring blood glucose data (SMBG) is a key tool for structured assessment of blood glucose, hypoglycaemia and hyperglycaemia rates. It can play an important role in guiding therapeutic decisions.

Healthcare professionals (HCP) struggle with time constraints, and may not have the opportunity to systematically download and review SMBG data. In addition, some analyses and reports may not be sufficiently useful or easy to understand, resulting in different HCPs interpreting the same data in fundamentally different ways.

SUMMARY

According to a first aspect, this specification discloses a computer implemented blood glucose analysis method comprising: receiving a plurality of blood glucose measurements relating to an individual taken over a plurality of temporal frames; identifying hypoglycaemic and/or hyperglycaemic blood glucose measurements in the plurality of blood glucose measurements; identifying a plurality of sub-intervals of the temporal frames in which there are a number of hypoglycaemic and/or hyperglycaemic blood glucose measurements that satisfies a threshold condition; inferring a temporal relationship between blood glucose measurements in a first sub-interval of the identified sub-intervals and blood glucose measurements in a second sub-interval of the identified sub-intervals; outputting the identified one or more sub-intervals of the temporal frames; and outputting a suggested causal driver for the inferred temporal relationship.

The plurality of temporal frames may be consecutive.

The plurality of temporal frames may each have a duration of a day and the sub-interval may be at most a three hour period. The plurality of temporal frames may each have a duration of a week and the sub-interval may be at most a day.

The method may further comprise plotting the blood glucose measurements from each of the plurality of temporal frames to generate a blood glucose measurement graph. Outputting the identified one or more sub-intervals of the temporal frames may comprise outputting the blood glucose measurement graph, wherein the determined one or more sub-intervals of the modal time period are highlighted in the blood glucose measurement graph. Plotting the blood glucose measurements from each of the plurality of temporal frames may comprise overlaying the blood glucose measurements from each of the plurality of temporal frames to generate a modal time period.

Threshold condition may be a number and/or density of hypoglycaemic and/or hyperglycaemic blood glucose measurements within a sub-interval.

Inferring a temporal relationship between the blood glucose measurements in the first sub-interval and the blood glucose measurements in the second sub-interval may comprise: determining matching pairs of blood glucose measurements, wherein a matching pair comprises a blood glucose measurement in the first sub-interval and a blood glucose measurement in the second sub-interval; determining if the total number of matching pairs exceeds a threshold condition; and in the event of a positive determination, inferring a temporal relationship between the determined trends that comprise the identified pattern.

Determining matching pairs of blood glucose measurements may comprise: comparing time stamps associated with the blood glucose measurements in the first sub-interval to time stamps associated with the blood glucose measurements in the second sub-interval; determining a matching pair if a time stamp associated with a blood glucose measurement in the first sub-interval correspond to a time stamp associated with a blood glucose measurement in the second sub-interval.

The method may further comprise: determining a time lag between the first sub-interval and the second sub-interval; and if the time lag is above a threshold time period, indicating that there is no temporal relationship between the first sub-interval and the second sub-interval.

The method may further comprise: receiving additional data relating to the individual taken over the plurality of temporal frames; and determining the suggested causal driver for the identified one or more sub-intervals of the temporal frames based at least in part on the additional data. The additional data may comprise one or more of: insulin dose data; data relating to exercise performed by the user; food intake data; and/or physiological measurements/data.

According to a second aspect, this specification describes apparatus comprising: one or more processors; and a memory, where in the memory comprises computer readable instructions that, when executed by the one or more processors, cause the apparatus to perform any of the methods described herein.

According to a third aspect, this specification describes a computer program product comprising computer readable code that, when executed by a computer, cause the computer to perform any of the methods described herein.

BRIEF DESCRIPTION OF THE FIGURES

Example embodiments will now be described by way of non-limiting example with reference to the accompanying drawings, in which.

DETAILED DESCRIPTION

Interpretation of self-monitoring blood glucose data (SMBG) data patterns can shed light on the reasons for poor glycaemic control and suggest possible management strategies. It is desirable to provide HCPs with tools that maximize the utility of SMBG data, by promptly highlighting and interpreting patterns that may otherwise remain unidentified. That will also help maintain patients' motivation to test regularly their blood glucose (BG) levels.

Typically, the average frequency of self-monitoring blood glucose measurements can be in the region of 0.5 blood glucose measurements per day in patients that are not treated with insulin and between 1 and 2 blood glucose measurements per day for patients treated with insulin. The pattern recognition method and systems described herein can be used to analyse such sparse data to provide clinically useful information for a user, such as a healthcare professional monitoring blood glucose levels in a patient. Implementation of the pattern recognition method and systems described herein in routine clinical practice, together with pattern causes prompts, may support treatment decisions and patient education, thus minimizing the risk of hypoglycaemia, hyperglycaemia and excessive blood glucose fluctuations.

Figure 1:
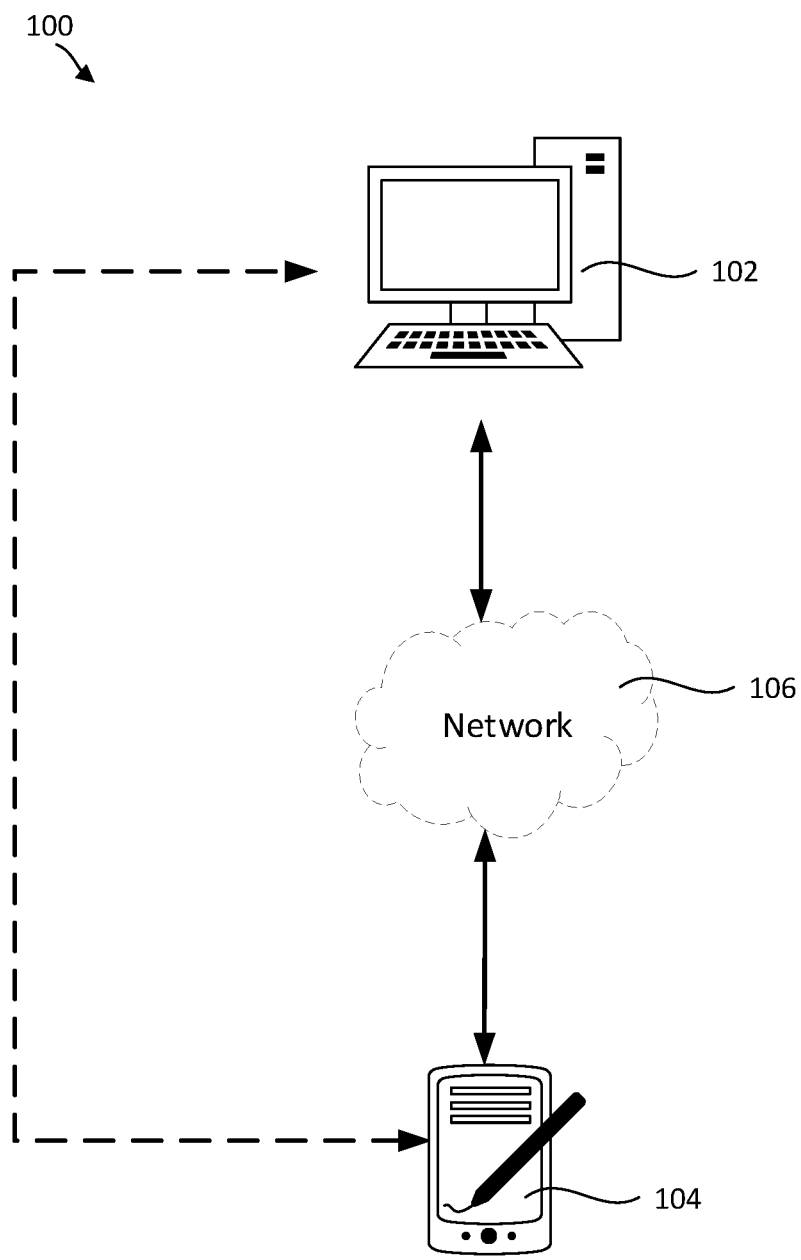
FIG. 1 shows an example of a system for analysing blood glucose measurements.

FIG. 1 illustrates an example of a system 100 for analysing blood glucose measurements.

The system comprises a user computing device 102 that is configured to receive blood glucose measurement relating to an individual/a patient. The user device 102 is configured to analyse blood glucose measurements and identify clinically relevant blood glucose patterns in the blood glucose measurements over a given time period. The user device 102 may be configured to identify temporal relationships between sets of blood glucose measurements. In some embodiments, the time period may be a modal time period. The user device 102 is configured to provide suggestions for potential causal drivers of the blood glucose levels of an individual/patient based on the received blood glucose measurements.

Figure 2:
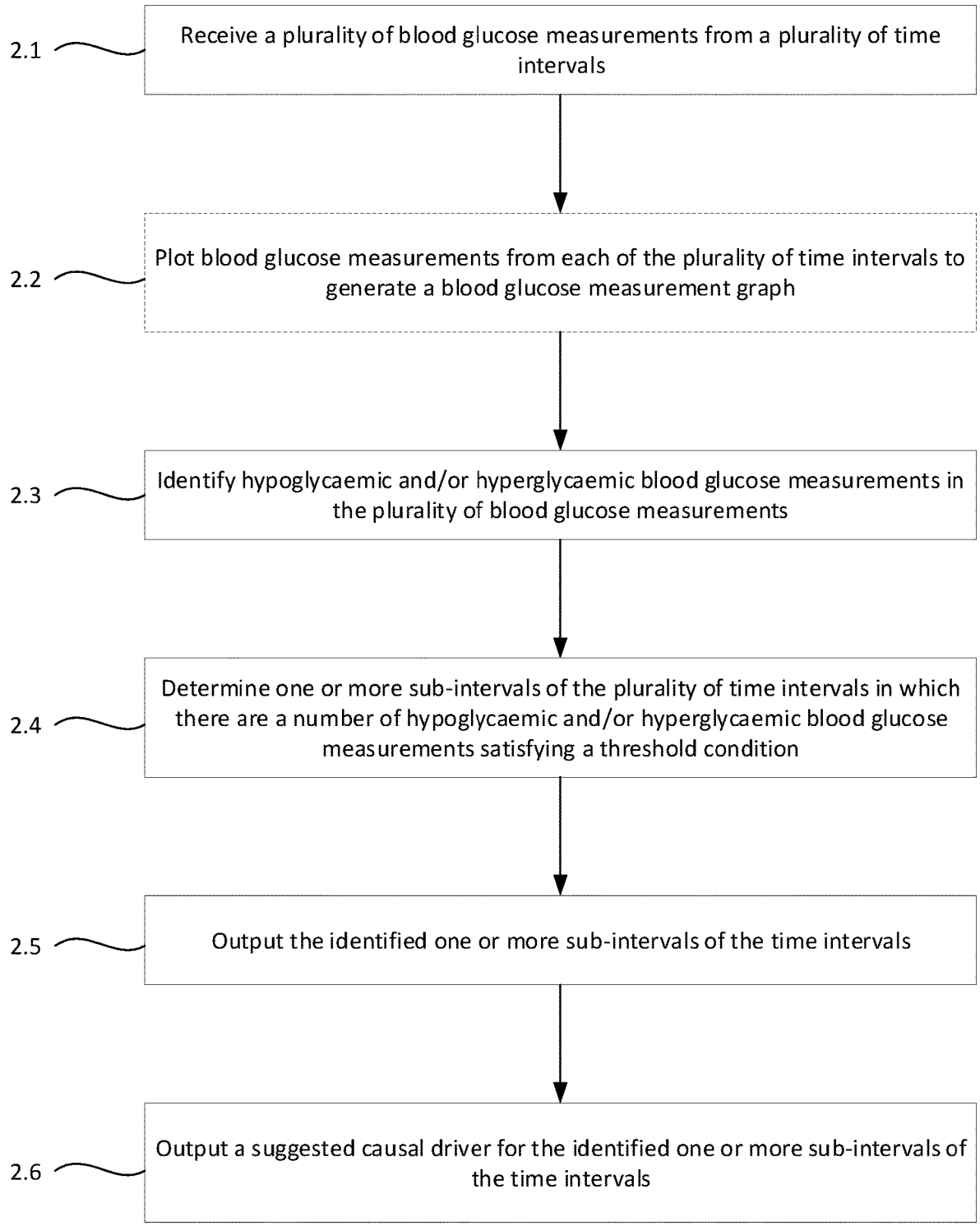
FIG. 2 shows a flow diagram of an example of a blood glucose analysis method.

The user device 102 is configured to perform any of the methods described herein, for example as described in relation to FIG. 2. The methods may be performed by one or more applications running on the user device 102.

The user device 102 may, for example, be any of: a mobile device, such as a mobile phone or tablet computer; a personal computer; a laptop; a personal digital assistant; a "smart" device; and/or a dedicated blood glucose monitoring device. An example of such a user device 102 is described below in relation to FIG. 6.

The user of the user device 102 may, in some embodiments, be a Healthcare Professional (HCP). In other embodiments, the user may be the individual/patient from whom the blood glucose measurements were taken. Different information and/or suggestions may be provided based on whether the user is an HCP using the system to assist in the optimisation of a patient's treatment, or if the user is the patient using the system to self-monitor their blood glucose measurements. For example, a patient using the system to self-monitor may be provided with a simpler interface that covers a shorter period of time (e.g. a day) when compared to that of an HCP, with the suggested causal drivers being limited to the narrow time frame, being more contextual and/or being provided at a more general level (e.g. "I see you have had a few hypos this week—has something changed in your therapy/meal times/etc. I can suggest XXX" or "I notice you are taking your insulin about 30 mins after your meal. For best blood glucose control, I can suggest taking the insulin at the start of the meal"). By contrast, an HCP may be provided with historical trend data over a longer period of time (e.g. several weeks or months) and/or data relating to modal time periods (e.g. modal days or weeks).

The suggested causal drivers provided to the HCP may cover a wider range of potential causal drivers and be more detailed than those provided to a patient. Accordingly, the same, similar, or different messages may be provided based on whether the user is the patient or the HCP.

The system may further comprise one or more blood glucose measurement devices 104. The blood glucose measurement devices 104 are operable to test the blood glucose levels of a patient. The blood glucose level may be recorded by the blood glucose measurement device 104 and sent to the user device 102. This blood glucose measurement data may be transferred to the user device 102 via a network 106. The network may, for example, be the internet and/or a local area network. Alternatively or additionally, the blood glucose measurement can be manually input to the user device 102, for example through a graphical user interface. In some embodiments, the blood glucose measurements may be transmitted directly from the blood glucose measurement devices 104, for example via a USB connection between a blood glucose device 104 and the user device. The blood glucose data may be transferred to the user device 102 via a separate "hub" device.

The user device 102 may further be configured to receive additional data relating to a patient. Examples of such additional data include: details of medicaments taken by the patient; insulin doses taken by the patient; data relating to exercise performed by the patient, for example collected by activity trackers; food intake of the patient; and/or other physiological measurements relating to the patient. The additional data may be used to refine the suggestions for potential causal drivers of the blood glucose levels of a patient. For example, hypoglycaemic/hyperglycaemic events may be correlated with insulin doses, indicating that the insulin dosage for the patient is not correct.

FIG. 2 shows a flow diagram of an example of a blood glucose analysis method. The method may be implemented by a computing device/system comprising one or more processors and a memory containing computer readable instructions that, when executed by the one or more processors, cause the computing device/system to perform the method.

At operation 2.1, a plurality of blood glucose measurements relating to a patient taken over a plurality of temporal frames are received.

The blood glucose measurements may be received at a user device 102 from a blood glucose measurement device 104, for example over a network. Alternatively or additionally, the blood glucose measurements may be input into the user device 102 manually by a user. The blood glucose measurements may be received continuously (i.e. as each measurement is taken). Alternatively, the blood glucose measurements may be received as a batch of blood glucose measurements.

Each blood glucose measurement is associated with a timestamp, indicating a date and time that the blood glucose measurement was taken. Each blood glucose measurement is further associated with a respective patient from whom the measurements were taken.

Temporal frames each comprise an interval of time. The temporal frames may each be of equal duration. For example, the temporal frames may be a day, a week or a month in duration. The temporal frames may be consecutive time intervals, such as a consecutive sequence of days or weeks. In some embodiments, the total period of time covered by the plurality of temporal frames is at most four weeks. This is typically the maximum time period over which a patient can reliably recall information associated with blood glucose measurements, such as contextual information relating to when, how and/or why the blood glucose measurement was taken. This can allow a healthcare professional to confirm hypotheses about the patient based on the collected blood glucose measurements.

In some embodiments, additional data relating to the patient taken over the plurality of temporal frames is received. Examples of such additional data include: insulin doses taken by the patient; data relating to exercise performed by the patient, for example collected by activity trackers or manually input by the patient; food intake of the patient; and/or other physiological measurements relating to the patient. The additional data may be used to refine the suggestions for potential causal drivers of the blood glucose levels of a patient. For example, hypoglycaemic/hyperglycaemic events may be correlated with insulin doses, indicating that the insulin dosage for the patient is not correct.

At optional operation 2.2 the blood glucose measurements from each of the plurality temporal frames are plotted to generate a blood glucose measurement graph.

In some embodiments, plotting the blood glucose measurements from each of the plurality temporal frames may comprise overlaying the blood glucose measurements from each of the plurality temporal frames to generate a modal time period.

A modal time period comprises all the blood glucose measurements for a set of equal time periods (i.e. the temporal frames) overlapped into a single copy of the equal time period. It may be thought of as a stack of the blood glucose measurements from the plurality of temporal frames. For example, the modal time period may comprise a first set of blood glucose measurements taken during a first temporal frame/time interval, overlaid by a second set of blood glucose measurements taken during a second, non-overlapping temporal frame/time interval of equal duration to the first temporal frame/time interval. Further blood glucose measurements from additional, distinct temporal frames may be overlaid on the first and second sets of blood glucose measurements to create the modal time period.

For example, a set of blood glucose measurements comprising blood glucose measurements taken over a plurality of days are overlapped to form a modal day. An example of a modal day is described in relation to FIG. 3. In another example, a set of blood glucose measurements comprising blood glucose measurements taken over a plurality of weeks are overlapped to form a modal week. An example of a modal week is described in relation to FIG. 4.

In some embodiments, plotting the blood glucose measurements from each of the plurality temporal frames may comprise plotting the blood glucose measurements over a continuous time period to generate a trend graph.

Figure 5:
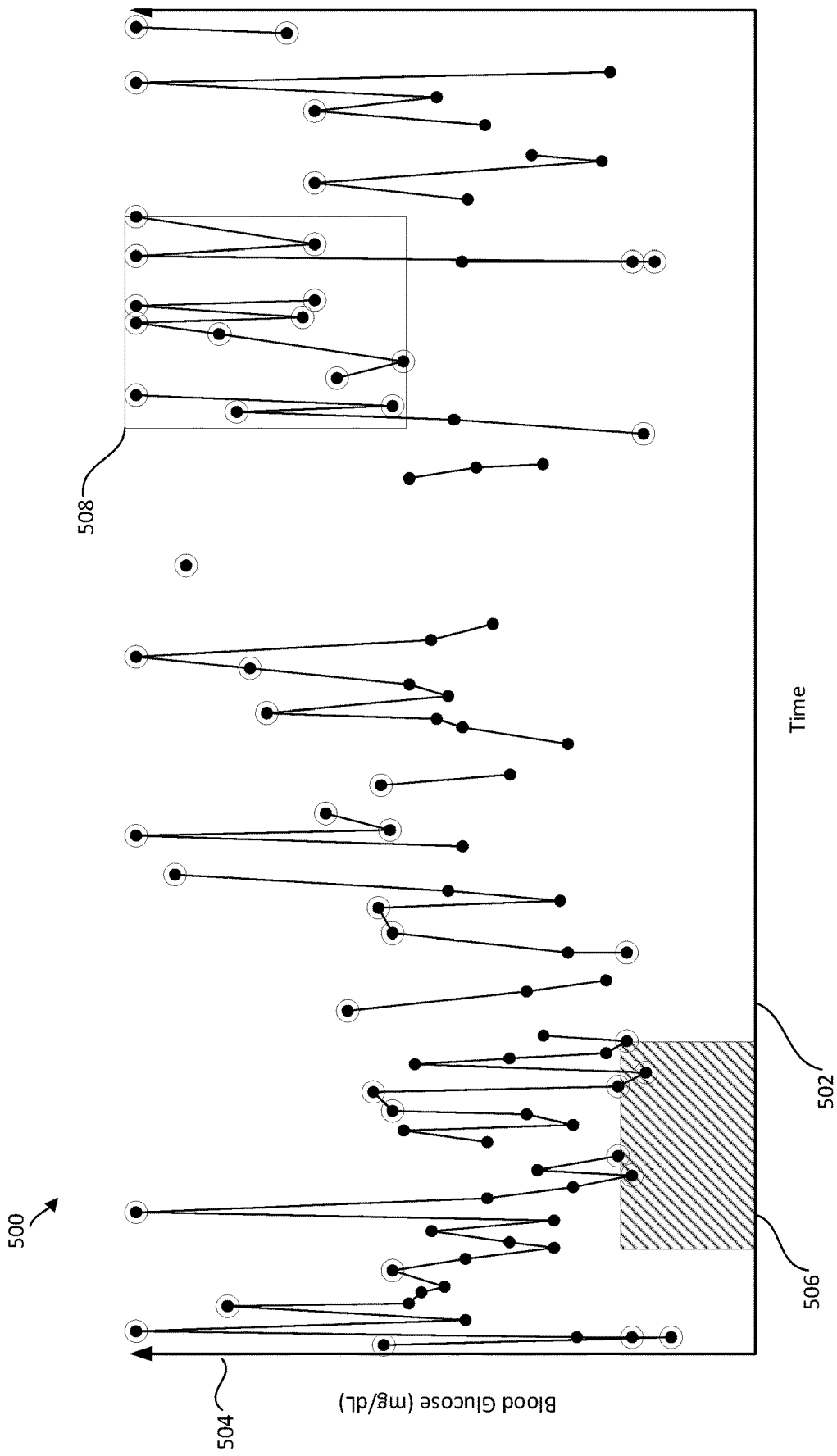
FIG. 5 shows an example of a historic trend graph of blood glucose measurements.

A historic trend chart comprises a plot of the blood glucose measurements from the temporal frames arranged in sequence. It displays a history of the patient blood glucose measurements. An example of a historic trend chart is shown in FIG. 5. The historic trend chart shows a plot of the blood glucose measurements over a range of time. In the historic trend graph, the average of hyper/hypo glycaemia event recurrence may be calculated within a given time period, e.g. three months. The weeks with a higher number of recurrences may be highlighted, i.e. it identifies the weeks in which the average number of hypoglycaemic and hyperglycaemic events exceeds the weekly average.

At operation 2.3, hypoglycaemic and/or hyperglycaemic blood glucose measurements in the plurality of blood glucose measurements are identified.

Hypoglycaemic blood glucose measurements comprise blood glucose measurements that fall below a hypoglycaemic threshold blood glucose value. The hypoglycaemic threshold value may be chosen in dependence on the patient whose blood glucose is being monitored. For example, the threshold may be a blood glucose value in the range 60-90 mg/dl. An example of a hypoglycaemic threshold value is 70 mg/dl (3.9 mmol/L). Further threshold values will be familiar to the skilled person. Blood glucose measurements in the modal time period are compared to the hypoglycaemic threshold, and any blood glucose measurements with a value below the hypoglycaemic threshold are identified as hypoglycaemic blood glucose measurements.

Hyperglycaemic blood glucose measurements comprise blood glucose measurements that are higher than a hyperglycaemic threshold blood glucose value. The hyperglycaemic threshold value may be chosen in dependence on the patient whose blood glucose is being monitored. For example, the threshold may be a blood glucose value in the range 160-220 mg/dl. An example of a hyperglycaemic threshold value is 180 mg/dl (10 mmol/L). Further threshold values will be familiar to the skilled person. Blood glucose measurements in the modal time period are compared to the hyperglycaemic threshold, and any blood glucose measurements with a value above the hyperglycaemic threshold are identified as hyperglycaemic blood glucose measurements.

At operation 2.4, one or more sub-intervals of the temporal frames in which there are a number of hypoglycaemic and/or hyperglycaemic blood glucose measurements that satisfies a threshold condition are determined.

In embodiments where a modal time period is used, the method uses the concept of recurrence to identify trends in the blood glucose measurements. Repetition of hyperglycaemic and/or hypoglycaemic blood glucose measurements in a sub-interval/sub-intervals of the modal time period can be used to indicate a trend/pattern in the blood glucose measurements. A sub interval of the modal day satisfying the threshold condition is referred to herein as a "relevant sub-interval" of the modal time period. Modal time periods assume that there is a certain "repeatability" in patient behaviour across a modal time period. This is why patterns are identified in similar times of the day/days of the week.

Historic trend chart aims to identify specific sub-intervals of (e.g. weeks/periods) in the recent weeks/months of the patient blood glucose history where a pattern may be present. These do not rely not imply "repeatability", but rather, may be an opportunity for the Healthcare Provider to work with the patient to identify the causal driver and address it together—either in terms of adaptation to the Rx or behaviour change.

The sub-intervals may be a fixed period of time. For example, a modal day may be use sub-intervals of up to three hours. In general, the modal time period may use sub-intervals of any relevant length. The fixed sub-interval may be used as a rolling window to identify relevant sub-intervals, i.e. sub-intervals that meet the threshold conditions.

In further examples, a modal week may look at a week day with a rolling period of time on that week day. The rolling period of time may be, for example, a 3 hour window. For example, if the modal time period is a day, the time period may be three hours, with a rolling window of one minute.

Patterns in the blood glucose measurements are recognised by identifying sub-intervals of time in the modal time period or historic blood glucose measurements in which a threshold condition is met, i.e. relevant sub-intervals. The threshold condition may be a threshold number of hypoglycaemic and/or hyperglycaemic blood glucose measurements within a sub-interval of time of a given length.

For example, a relevant sub-interval may be identified when at least two hypoglycaemic blood glucose measurements are identified within a period of time in the modal time period of up to three hours. Alternatively or additionally, a relevant sub-interval may be identified when at least three hyperglycaemic blood glucose measurements are identified within a period of time in the modal time period of up to three hours.

The threshold condition may alternatively or additionally comprise a density threshold. If the density of hypoglycaemic and/or hyperglycaemic blood glucose measurements in a sub-interval is higher than a threshold density, then the sub-interval may be identified as a relevant sub-interval. The threshold density may be based on an average density of hypoglycaemic and/or hyperglycaemic blood glucose measurements in the modal day. For example, a relevant sub-interval may be detected when the density of hypoglycaemic and/or hyperglycaemic blood glucose measurements is significantly higher in relation to the total of the glucose values in the same period. A threshold density may be set based on the average density for the time period. The threshold density may the average density multiplied by a number greater than one, e.g. 150% of the average density. It may be calculated by moving the window forward one observation at a time.

As an illustrative example, the method may identify three sub-intervals within the temporal frames with more than two hypoglycaemic values, e.g. sub-interval 1:5 hypo-values (2.5 hours long), sub-interval 2:2 values (3 hours long), and sub-interval 3:4 hypo-values (3 hours long). The density of those values is compared to the average hypoglycaemic density for the day. If, for example, the total number of hypo values for the day is 20 (i.e. 11 are in sub-intervals, and 9 are not). It will then determine a density of 20/24 hypo-events per hour. These are compared with the density in the sub-intervals.

In this example, the density in the three sub-intervals will be respectively: 2, 0.67 and 1.33. Based on threshold density (which may be set by the user/HCP), the system may highlight sub-intervals 1 and 3 as patterns, and omit sub-interval 2, as its density (0.67 events/hour) is lower that the daily density.

A factor may be applied to the average density (e.g. 130%, 140%, 150% etc) by which the sub-interval density must be higher than the average daily density, to consider a sub-interval a pattern; this may be in addition to the absolute number of events in a sub-interval satisfying a threshold number (e.g. 2 hypoglycaemic or 3 hyperglycaemic events).

Repeated measurements taken within a short time period of each other with a temporal frame can reduce the reliability of relevant sub-intervals of the modal day and trends identified using recurrence. In some embodiments, measurements taken in the same time interval that are within a threshold period of each other in real time are treated as a single event for the purpose of determining the sub-intervals of the modal time period in which there are a number of hypoglycaemic and/or hyperglycaemic blood glucose measurements that satisfies a threshold condition. For example, two or more blood glucose measurements taken within half an hour of each other may be treated as a single event/measurement.

In some embodiments, both a threshold number and threshold density of blood glucose measurements are required to be satisfied in order to identify a relevant sub-interval.

Further analysis may be performed on the blood glucose measurements in the modal time period/temporal frames to identify patterns. For example, temporal relations between identified sub-intervals may be identified. These may be used to infer causal relations between patterns of hypoglycaemic and/or hyperglycaemic blood glucose measurements, and to suggest possible causal drivers.

At operation 2.5, the determined one or more sub-intervals of the modal time period are output. The identified relevant sub-intervals may be output in a graph of the modal time period, with the relevant sub intervals highlighted. Examples of such output are provided in FIGS. 3-5. The relevant patterns of hypoglycaemia and/or hyperglycaemia, based on the absolute and relative frequency of these events, and may be overlaid on reports that a healthcare professional is already using to analyse blood glucose measurements.

At operation 2.6, a suggested causal driver for the identified one or more sub-intervals of the temporal frames and/or the identified patterns is output.

Suggestions are provided to the HCP/patient for what the causal driver of the identified one or more sub-intervals of the temporal frames and/or the identified patterns may be. These may comprise areas to focus on in a discussion with the patient—e.g. potential reasons that may be causing these blood glucose patterns. Patients may be provided with messages related to the identified one or more patterns, along with potential suggestions based on the identified patterns. For example, a patient may be provided with suggestions on how to adjust their daily routine based on the identified patterns. Messages provided to the patient may relate to, for example, individual events, patterns of data spanning days or weeks, at certain time frames within the day.

The suggestions may be provided through an interactive graph of the blood glucose measurements (e.g. a graph of the modal time period or the historical trend chart). For example, the HCP may select an identified pattern on the graph via an interactive user interface of the user device 102. A pop-up window may appear offering the HCP selectable options that relate to the patient therapy. For example, the HCP may select basal-only, orals meds, basal-bolus, etc.

Based on the identified patterns/identified sub intervals (and the information input by the HCP) the system shows a list of potential reasons that may be causing the pattern. For example, the HCP may be provided with a message through the user interface of the user device 102. As an example, the message may "During the [4-week] period or shortly before, were there any:
   therapy changes or irregularities, e.g. new prescription, higher basal insulin dose, changing injection times
   lifestyle changes or irregularities, e.g. more exercise/walk, skipping meals, especially at dinner time
   others, e.g. shift work"

For patients, the suggestions will be provided as contextual messages, such as "I notice you are taking your insulin about 30 mins after your meal. For best blood glucose control, I can suggest taking the insulin at the start of the meal", for example. The contextual messages may be based on the additional information provided relating to the patient, e.g. meal times, exercise times and duration, and/or insulin dose times and values.

The suggested causal drivers may be provided based on the type of temporal relationship identified in the blood glucose measurements. A database of potential temporal relationships and associated causal drivers may be provided. The database may be used to match the identified temporal relationship with one or more causal drivers. Alternatively or additionally, a default set of causal drivers may be provided. The default set may, in some embodiments, be reverted to if no matching temporal relationship is found in the database.

The suggested causal drivers may be provided based at least in part on any additional data provided. For example, patterns in the additional data may be identified and/or matched to corresponding blood glucose measurements based on timestamps of the additional data. Based on the type of additional data and its values, a casual driver of the blood glucose measurements may be suggested. Such causal drivers may, for example, include: an incorrect insulin dose; dietary factors; meal times; over/under eating; an excess/lack of exercise; and/or an underlying physiological condition.

As mentioned above in relation to operation 2.4, further analysis may be performed on the blood glucose measurements in the modal time period to identify patterns. For example, temporal relations between patterns and trends may be identified. These may be used to infer causal relations between patterns of hypoglycaemic and/or hyperglycaemic blood glucose measurements.

For example, based on the identified relevant sub-intervals, patterns of hypo-hyper, hyper-hypo, hypo-hypo and/or hyper-hyper blood glucose measurements can be identified in the modal time period. These patterns comprise a first pattern of a hypoglycaemic or hyperglycaemic event in a first relevant sub-interval followed by a second pattern of a hypoglycaemic or hyperglycaemic event in a second relevant sub interval.

To identify a pattern between two relevant sub-intervals, a plurality of hypoglycaemic or hyperglycaemic blood glucose measurements in a first sub-interval of the temporal frames may be identified. A plurality of hypoglycaemic or hyperglycaemic blood glucose measurements in a second sub-interval of the temporal frames may then be identified. The time stamps associated with the blood glucose measurements in the first sub-interval are compared to the time stamps associated with the blood glucose measurements in the second sub-interval. If the time stamps for any pair of blood glucose measurements (one from the first sub-interval and one from the second sub-interval) correspond (e.g. they are taken from the same day), then those two measurements are matched. If the total number of matches is above a threshold value, then a pattern is identified. The threshold value may, for example, be a fraction of the total number of blood glucose measurements in the first or second sub-interval (e.g. 50%).

For example, in a modal day the system may identify a first relevant sub-interval with 4 hypo-values in the period 8-10 am. Then a second relevant sub-interval with 5 hyper-values in the period 11-1 pm is identified. The system then looks at how many of the values in the first sub-interval have a corresponding "match" in the second sub-interval. If this number meets a threshold condition then there is a correlation between the hypo pattern and the hyper pattern; and the system can infer that it is likely the hypo pattern that is causing the hyper pattern.

In other words identified relevant sub-intervals in blood glucose measurements may be processed in order to determine if the constituents of the pattern have a causal relationship, i.e. if there is a causal relationship between the first sub-interval and the second sub-interval. For example, at first glance of the modal time period, patterns may appear as inter-related, but in reality, the blood glucose measurements may be part of different temporal frames.

The identified patterns are checked to see if the first relevant sub-interval and second relevant sub-interval correspond in time. If blood glucose measurements in the first relevant sub-interval originate from the same temporal frame as the blood glucose measurements in the second relevant sub-interval, then a causal/temporal relationship may be established between the two sub-intervals.

For example, the method may comprise attempting to pair blood glucose measurements in the first sub-interval with blood glucose measurements in the second sub-interval, based on whether the blood glucose measurements in the second sub-interval are taken from the same temporal frame as the measurement in the first sub-interval. If a threshold number of pairs are made, a temporal/causal relationship between the two sub-intervals is identified. The threshold number may for example, be a fixed number, or may be a fraction of the number of blood glucose measurements in the first sub-interval or second sub-interval.

Once a temporal relationship has been identified, it may be highlighted in a representation of the modal time period. For example, an outline may be provided on a graph of the modal day.

Determining a temporal relationship between two or more patterns may further comprise determining a time lag between two of the sub-intervals; and if the time lag is above a threshold time period, indicating that there is no temporal relationship between the two sub-intervals. For example, if the first sub-interval spans a first time, and the second sub-interval spans a second time, the time lag may be calculated from the difference between the time at the end of the first sub-interval and the time at the start of the second sub-interval, or vice versa depending on the temporal ordering of the sub-intervals.

Figure 3:
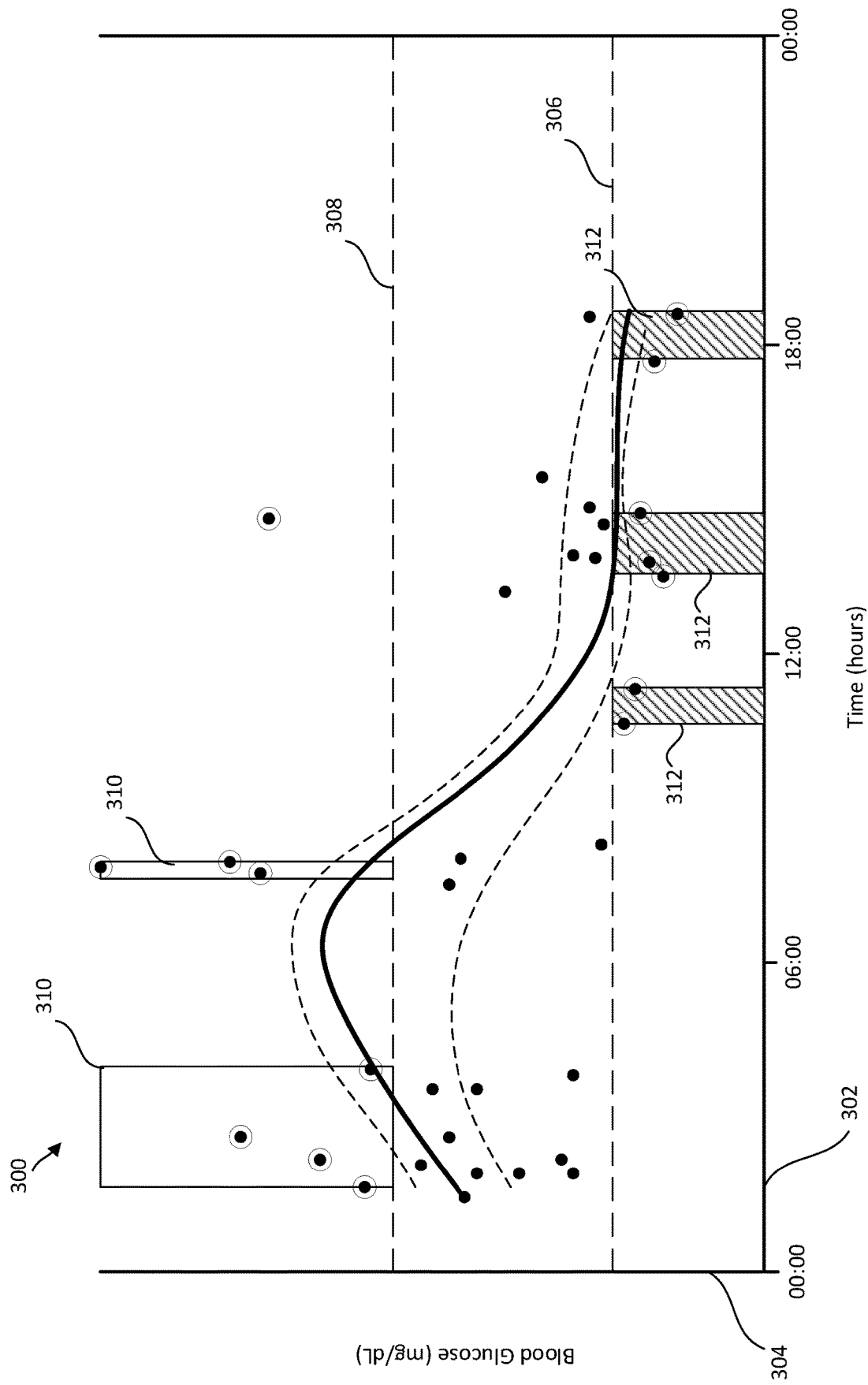
FIG. 3 shows an example of a modal day of blood glucose measurements.

FIG. 3 shows an example of a modal day of blood glucose measurements. The modal day is represented as a graph 300. Time is represented along the x-axis 302, with blood glucose measurement value represented along the y-axis 304. The graph 300 comprises a plurality of blood glucose measurements taken from a set of temporal frames. Each temporal frame is a day in duration. The temporal frames have been overlaid to generate the modal day.

The hypoglycaemic blood glucose threshold 306 is indicated by the lower dashed line. Blood glucose measurements below this line are identified as hypoglycaemic blood glucose measurements.

The hyperglycaemic blood glucose threshold 308 is indicated by the upper dashed line. Blood glucose measurements above this line are identified as hyperglycaemic blood glucose measurements.

Relevant hyperglycaemic sub-intervals are indicated by the shaded regions 310 around clusters of hyperglycaemic blood glucose measurements. Relevant hypoglycaemic sub-intervals are indicated by the hatched regions 312 around clusters of hypoglycaemic blood glucose measurements.

The patterns highlight the times of day when the patient has more frequent hypo- (e.g. <70 mg/dl) or hyperglycaemic (e.g. >180 mg/dl) episodes, that may be linked to the patient's daily routine. The occurrence is calculated over a period of up to 4 weeks. A pattern is detected when at least 2 hypoglycaemic or 3 hyperglycaemic blood glucose measurements are identified in a period of up to 3 hours, and/or the density of hypoglycaemic or hyperglycaemic blood glucose measurements is higher than average.

A median blood glucose measurement line 314 is shown, along with a 75-percentile line 316 and a 25-percentile line 318.

Figure 4:
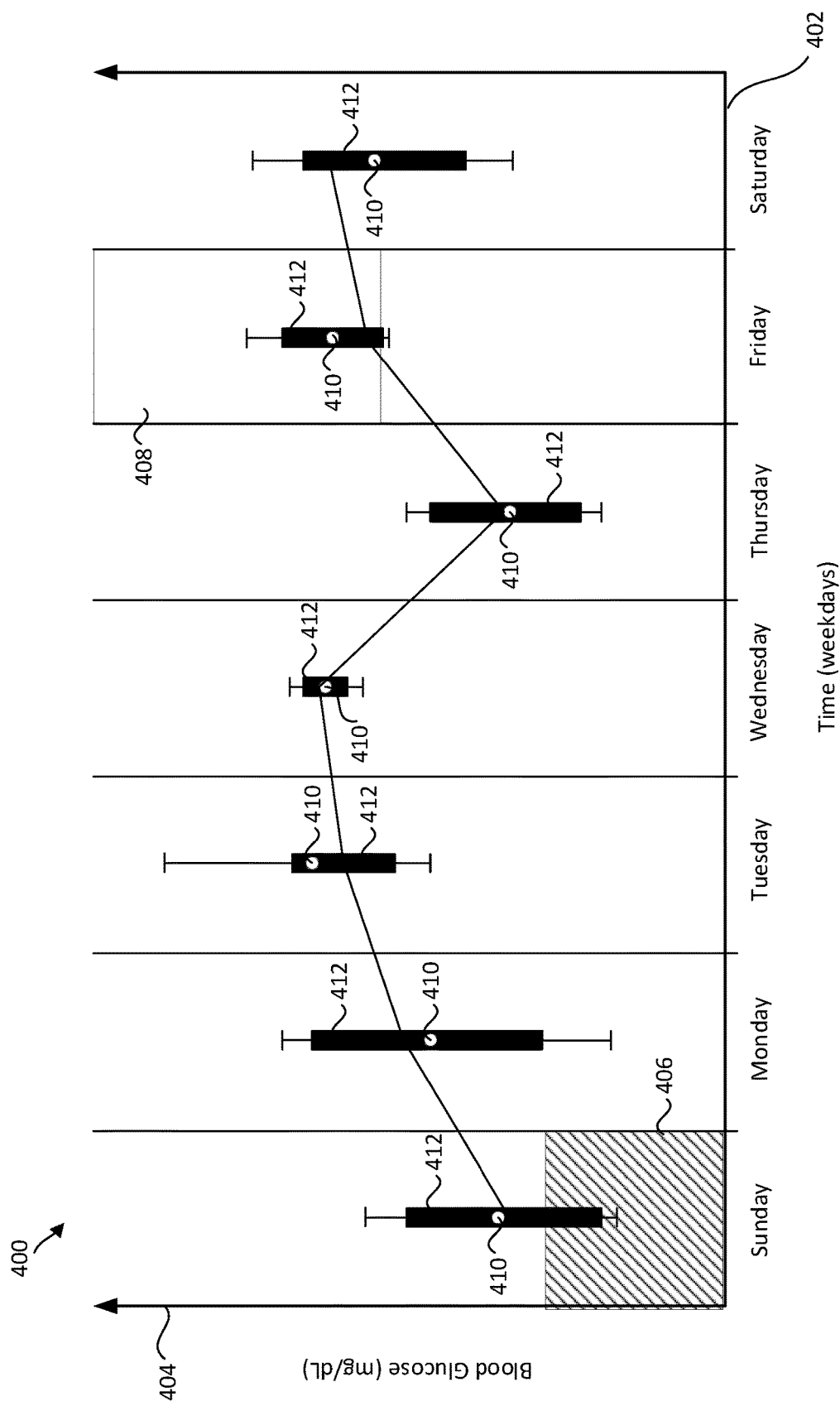
FIG. 4 shows an example of a modal week of blood glucose measurements.

FIG. 4 shows an example of a modal week of blood glucose measurements. The modal week is represented as a graph 400. Time is represented along the x-axis 402 in weekdays (e.g. Sunday to Saturday), with blood glucose measurement value represented along the y-axis 404.

A daily average 410 of the blood glucose measurements for the modal week is plotted for each day, along with a bar 412 representing the range around the average into which 50% of the blood glucose measurements for that day in the modal week fall. A line extending above and below from the bar indicates the 10-90% range of blood glucose measurements. The modal week also shows a median line 414.

Relevant sub-intervals 406, 408 are highlighted to show the days of the week when the patient has more frequent hypoglycaemic or hyperglycaemic episodes that may be linked to the patient's weekly routine. A pattern requires that hypoglycaemic or hyperglycaemic episodes occurrence is consistent on the same week day over several weeks, and that it is significantly higher on the same week day when compared to weekly averages.

FIG. 5 shows an example of a historical trend chart of blood glucose measurements. The historical trend chart is represented as a graph 500. Time is represented along the x-axis 502, with blood glucose measurement value represented along the y-axis 504. It displays a history of the patient blood glucose measurements. During a selected time period, it shows the weeks in which the average number of hypoglycaemic and hyperglycaemic events exceeds the weekly average.

The time axis spans a continuous period of time, such as one or more months or a plurality of weeks. Blood glucose measurements are shown as points in the graph, with hyperglycaemic and hypoglycaemic blood glucose values highlighted. Relevant sub-intervals 506, 508 of time are highlighted.

Figure 6:
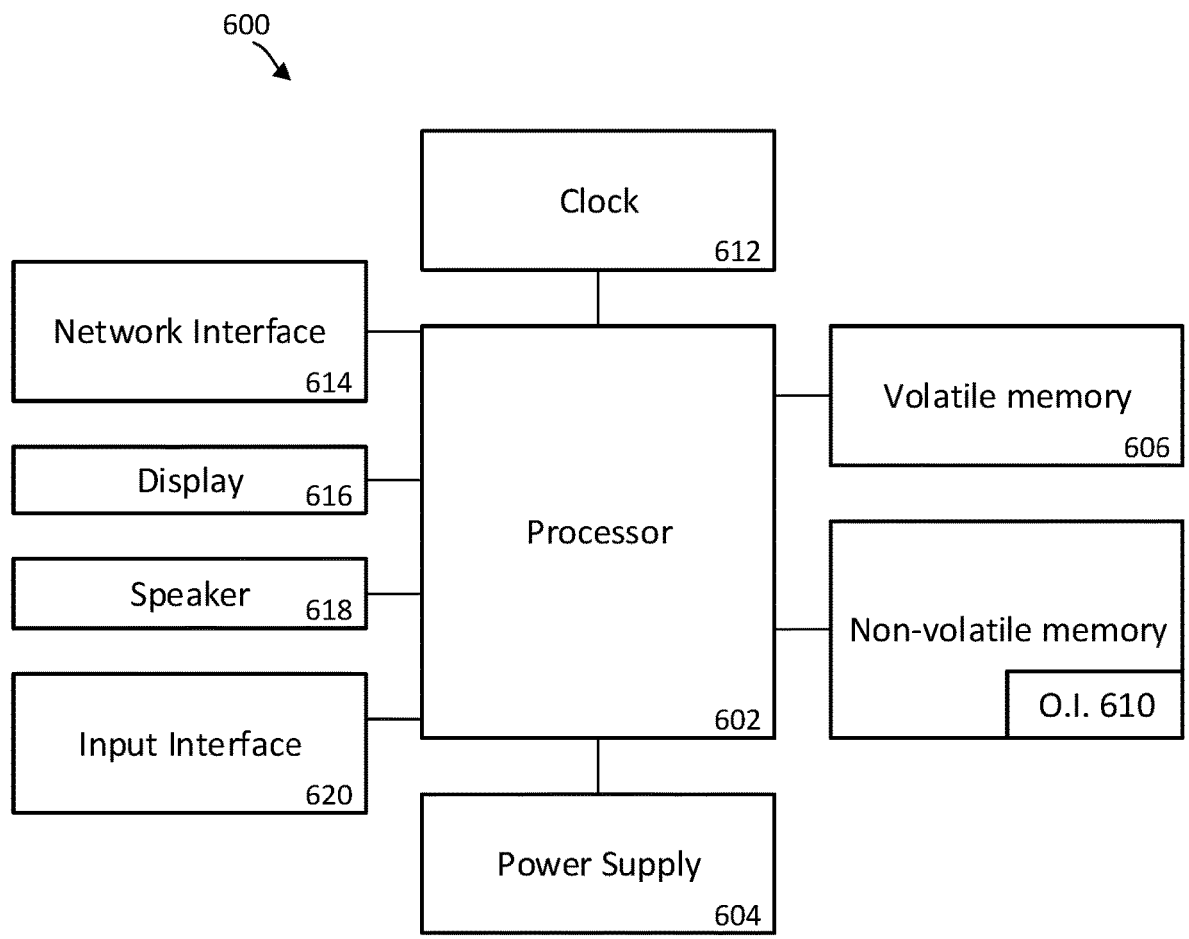
FIG. 6 shows example electronic circuitry of a user device.

FIG. 6 shows example electronic circuitry of a user device 102. The electronics system 600 of the user device 102 comprises the processor arrangement 202. The processor arrangement 602 and other hardware components may be connected via a system bus (not shown). Each hardware component may be connected to the system bus either directly or via an interface. A power supply 604 is arranged to provide power to the electronics system.

The processor arrangement 602 controls operation of the other hardware components of the electronics system 600. The processor arrangement 602 may be an integrated circuit of any kind. The processor arrangement 602 may for instance be a general purpose processor. It may be a single core device or a multiple core device. The processor arrangement 602 may be a central processing unit (CPU) or a general processing unit (GPU). Alternatively, it may be a more specialist unit, for instance a RISC processor or programmable hardware with embedded firmware. Multiple processors may be included. The processor arrangement 602 may be termed processing means.

The electronics system 600 comprises a working or volatile memory 606. The processor arrangement 602 may access the volatile memory 606 in order to process data and may control the storage of data in memory. The volatile memory 606 may be a RAM of any type, for example Static RAM (SRAM), Dynamic RAM (DRAM), or it may be Flash memory. Multiple volatile memories may be included, but are omitted from the Figure.

The electronics system comprises a non-volatile memory 608. The non-volatile memory 608 stores a set of operation instructions 610 for controlling the normal operation of the processor arrangement. The non-volatile memory 608 may be a memory of any kind such as a Read Only Memory (ROM), a Flash memory or a magnetic drive memory. Other non-volatile memories may be included, but are omitted from the Figure.

The processor arrangement 602 operates under the control of the operating instructions 610. The operating instructions 610 may comprise code (i.e. drivers) relating to the hardware components of the electronics system 600, as well as code relating to the basic operation of the user device. The operating instructions 610 may also cause activation of one or more software modules stored in the non-volatile memory 608. Generally speaking, the processor arrangement 602 executes one or more instructions of the operating instructions 610, which are stored permanently or semi-permanently in the non-volatile memory 608, using the volatile memory 606 temporarily to store data generated during execution of the operating instructions. The operating instructions may include computer readable instructions that, when executed by the processor arrangement 602, cause the user device to perform any of the methods described herein.

The processor arrangement 602, the volatile memory 606 and the non-volatile memory 608 may be provided as separate integrated circuit chips connected by an off-chip bus, or they may be provided on a single integrated circuit chip. The processor arrangement 602, the volatile memory 606 the non-volatile memory 608 may be provided as a microcontroller.

The electronics system 600 comprises a clock 612. The clock 612 may be a clock crystal, for example, a quartz crystal oscillator. The clock 612 may be a separate component to the processor arrangement 602 which is configured to provide a clock signal to the processor arrangement 602. The processor arrangement 602 may be configured to provide a real time clock based on the signal from the clock 612. Alternatively, the clock 612 may be a clock crystal which is provide on a single integrated circuit chip with the processor arrangement 602.

The electronics system 600 comprises one or more network interfaces 614. The network interfaces 614 facilitate the connection of the user device 102 to one or more computer networks and the bi-directional exchange of information between the user device 102 and other members of the networks. These networks may include the Internet, a Local Area Network, or any other network required by the user device to communicate with the data centre and/or contact centre. The network interfaces 614 comprise a network interface controller, such as an Ethernet adaptor, a Wi-Fi adaptor and/or a Bluetooth adaptor. The network interfaces 614 are associated with one or more network addresses for identifying the user device on the network. The one or more network addresses may be in the form of an IP address, a MAC address, and/or an IPX address. Other members of the network may include blood glucose measurement devices 104.

In some embodiments, the processor arrangement 602 in the user may not be sufficiently powerful to perform one or more of the functions described herein. Instead, the processing arrangement 602 is configured to communicate via the network interface with an additional computer system that has more computing power available to it. The processor arrangement 602 can transmit data from the user device to the additional computer system, where it can be processed using the additional computing power of the additional computer system. The additional computer system can return the results of this processing back to the processor arrangement for further processing. The additional computing system can, for example, be a remote computer system, a distributed computer system, or part of a data centre.

The electronics system 600 further comprises a display 616. The display 616 can be operated by the processing arrangement 602 via a display driver to provide a graphical user interface to a user. The display 616 may in the form of an LCD screen. The display 216 may alternatively be in the form of an LED screen. The display 616 provides status information to the user relating to the user device 102. Examples of such status information include which mode the user device is in, a battery status, a memory status, a network connection status and/or whether an external power supply is connected. The display 616 may provide the results of the method of FIG. 2, for example in the form of graphs in FIGS. 3-5.

The electronics system 600 may comprise a speaker 618. The speaker 618 is an example of an audio transducer. The speaker 618 can be operated to provide an audio output in the form of spoken word, or more generally any sound. The speaker 618 may provide audible feedback to the user relating to the use of the user device 102 and/or blood glucose measurement devices 104. An example of this would be an audible indication that a blood glucose measurement device 104 was running low on blood glucose testing material. In some embodiments, the speaker 618 may provide audible reminders to the user. For example, the speaker 618 may remind the user to take a scheduled dose of medication or record a blood glucose measurement.

The electronics system 600 further comprises one or more input interfaces 620. The input interfaces 620 allow a user to input data into the user device 102. Examples of input interfaces include a touch screen, a keyboard, a number pad, one or more dedicated buttons and/or a speech recognition engine.

Implementations of the methods described herein may be realised in digital electronic circuitry, integrated circuitry, specially designed ASICs (application specific integrated circuits), computer hardware, firmware, software, and/or combinations thereof. These may include computer program products (such as software stored on e.g. magnetic discs, optical disks, memory, Programmable Logic Devices) comprising computer readable instructions that, when executed by a computer, such as that described in relation to FIG. 6, cause the computer to perform one or more of the methods described herein.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin. Examples of insulin derivatives are, for example, B29-N-myristoyl-des(B30) human insulin, Lys(B29) (N- tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Any system feature as described herein may also be provided as a method feature, and vice versa. As used herein, means plus function features may be expressed alternatively in terms of their corresponding structure. In particular, method aspects may be applied to system aspects, and vice versa.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

The invention claimed is:

1. A computer implemented blood glucose analysis method comprising:
    receiving a plurality of blood glucose measurements relating to an individual taken over a plurality of temporal frames;
    identifying hypoglycaemic and/or hyperglycaemic blood glucose measurements in the plurality of blood glucose measurements;
    identifying a plurality of sub-intervals of the temporal frames in which there are a number of hypoglycaemic and/or hyperglycaemic blood glucose measurements that satisfies a threshold condition;
    inferring a temporal relationship between blood glucose measurements in a first sub-interval of the identified sub-intervals and blood glucose measurements in a second sub-interval of the identified sub-intervals, wherein inferring the temporal relationships comprises:
        determining a plurality of matching pairs of blood glucose measurements, wherein a matching pair comprises a blood glucose measurement in the first sub-interval and a blood glucose measurement in the second sub-interval and wherein determining matching pairs of blood glucose measurements comprises:
            comparing time stamps associated with the blood glucose measurements in the first sub-interval to time stamps associated with the blood glucose measurements in the second sub-interval; and
            determining a matching pair if a time stamp associated with a blood glucose measurement in the first sub-interval correspond to a time stamp associated with a blood glucose measurement in the second sub-interval,
        determining if the total number of matching pairs exceeds a threshold number of pairs, wherein the threshold number of pairs is equal to or more than two; and
        in the event of a positive determination, inferring a temporal relationship between the first sub-interval and the second sub-interval;
    outputting the identified one or more sub-intervals of the temporal frames; and
    outputting a suggested causal driver for the inferred temporal relationship, wherein the causal driver is selected from a database based on the inferred temporal relationship.

2. The method of claim 1, wherein the plurality of temporal frames are consecutive.

3. The method of claim 1, wherein the plurality of temporal frames each have a duration of a day and wherein the sub-interval is at most a three hour period.

4. The method of claim 1, wherein the plurality of temporal frames each have a duration of a week and wherein the sub-interval is at most a day.

5. The method of claim 1, further comprising plotting the blood glucose measurements from each of the plurality of temporal frames to generate a blood glucose measurement graph.

6. The method of claim 5, wherein outputting the identified one or more sub-intervals of the temporal frames comprises outputting the blood glucose measurement graph, wherein the identified one or more sub-intervals are highlighted in the blood glucose measurement graph.

7. The method of claim 5, wherein plotting the blood glucose measurements from each of the plurality of temporal frames comprises overlaying the blood glucose measurements from each of the plurality of temporal frames to generate a modal time period.

8. The method of claim 1, wherein the threshold condition is a number and/or density of hypoglycaemic and/or hyperglycaemic blood glucose measurements within a sub-interval.

9. The method of claim 1, further comprising:
    determining a time lag between the first sub-interval and the second sub-interval; and
    if the time lag is above a threshold time period, indicating that there is no temporal relationship between the first sub-interval and the second sub-interval.

10. The method of claim 1, further comprising:
    receiving additional data relating to the individual taken over the plurality of temporal frames; and
    determining the suggested causal driver for the identified one or more sub-intervals of the temporal frames based at least in part on the additional data.

11. The method of claim 10, wherein the additional data comprises one or more of: insulin dose data; data relating to exercise performed by the user; food intake data; and/or physiological measurements/data.

12. An apparatus comprising:
    one or more processors; and
    a memory, wherein the memory comprises computer readable instructions that, when executed by the one or more processors, cause the apparatus to:
        receive a plurality of blood glucose measurements relating to an individual taken over a plurality of temporal frames;
        identify hypoglycaemic and/or hyperglycaemic blood glucose measurements in the plurality of blood glucose measurements;
        identify a plurality of sub-intervals of the temporal frames in which there are a number of hypoglycaemic and/or hyperglycaemic blood glucose measurements that satisfies a threshold condition;
        infer a temporal relationship between blood glucose measurements in a first sub-interval of the identified sub-intervals and blood glucose measurements in a second sub-interval of the identified sub-intervals, wherein inferring the temporal relationships comprises:
            determining matching pairs of blood glucose measurements, wherein a matching pair comprises a blood glucose measurement in the first sub-interval and a blood glucose measurement in the second sub-interval and wherein determining matching pairs of blood glucose measurements comprises:
                comparing time stamps associated with the blood glucose measurements in the first sub-interval to time stamps associated with the blood glucose measurements in the second sub-interval; and determining a matching pair if a time stamp associated with a blood glucose measurement in the first sub-interval correspond to a time stamp associated with a blood glucose measurement in the second sub-interval, determining if the total number of matching pairs exceeds a threshold condition, wherein the threshold number of pairs is equal to or more than two; and in the event of a positive determination, inferring a temporal relationship between the first sub-interval and the second sub-interval;

output the identified one or more sub-intervals of the temporal frames; and output a suggested causal driver for the inferred temporal relationship, wherein the causal driver is selected from a database based on the inferred temporal relationship.

13. The apparatus of claim 12, wherein the memory further comprises computer readable instructions that, when executed by the one or more processors, cause the apparatus to plot the blood glucose measurements from each of the plurality of temporal frames to generate a blood glucose measurement graph.

14. The apparatus of claim 12, wherein the memory further comprises computer readable instructions that, when executed by the one or more processors, cause the apparatus to:

determine a time lag between the first sub-interval and the second sub-interval; and if the time lag is above a threshold time period, indicate that there is no temporal relationship between the first sub-interval and the second sub-interval.

15. The apparatus of claim 12, wherein the memory further comprises computer readable instructions that, when executed by the one or more processors, cause the apparatus to:

receive additional data relating to the individual taken over the plurality of temporal frames; and determine the suggested causal driver for the identified one or more sub-intervals of the temporal frames based at least in part on the additional data.

16. The apparatus of claim 15, wherein the additional data comprises one or more of: insulin dose data; data relating to exercise performed by the user; food intake data; and/or physiological measurements/data.

17. A non-transitory computer program product comprising computer readable code that, when executed by a computer, causes the computer to:

receive a plurality of blood glucose measurements relating to an individual taken over a plurality of temporal frames;

identify hypoglycaemic and/or hyperglycaemic blood glucose measurements in the plurality of blood glucose measurements;

identify a plurality of sub-intervals of the temporal frames in which there are a number of hypoglycaemic and/or hyperglycaemic blood glucose measurements that satisfies a threshold condition;

infer a temporal relationship between blood glucose measurements in a first sub-interval of the identified sub-intervals and blood glucose measurements in a second sub-interval of the identified sub-intervals, wherein inferring the temporal relationships comprises:

determining a plurality of matching pairs of blood glucose measurements, wherein a matching pair comprises a blood glucose measurement in the first sub-interval and a blood glucose measurement in the second sub-interval and wherein determining matching pairs of blood glucose measurements comprises:

comparing time stamps associated with the blood glucose measurements in the first sub-interval to time stamps associated with the blood glucose measurements in the second sub-interval; and determining a matching pair if a time stamp associated with a blood glucose measurement in the first sub-interval correspond to a time stamp associated with a blood glucose measurement in the second sub-interval, determining if the total number of matching pairs exceeds a threshold number of pairs, wherein the threshold number of pairs is equal to or more than two; and in the event of a positive determination, inferring a temporal relationship between the first sub-interval and the second sub-interval;

output the identified one or more sub-intervals of the temporal frames; and output a suggested causal driver for the inferred temporal relationship, wherein the causal driver is selected from a database based on the inferred temporal relationship.

* * * * *